United States Patent [19]

Ito

[11] 4,414,108
[45] * Nov. 8, 1983

[54] APPARATUS AND METHOD FOR CONTINUOUS COUNTERCURRENT EXTRACTION AND PARTICLE SEPARATION

[75] Inventor: Yoichiro Ito, Bethesda, Md.

[73] Assignee: The United States of America as represented by the Department of Health and Human Services, Washington, D.C.

[*] Notice: The portion of the term of this patent subsequent to Apr. 13, 1999 has been disclaimed.

[21] Appl. No.: 315,271

[22] Filed: Oct. 26, 1981

Related U.S. Application Data

[62] Division of Ser. No. 148,491, May 9, 1980, Pat. No. 4,324,661.

[51] Int. Cl.$^3$ .............................................. B01D 15/08
[52] U.S. Cl. .................................. 210/198.2; 210/927
[58] Field of Search ............... 210/634, 635, 657, 782, 210/198.2, 511, 927; 233/16, 24, 27

[56] References Cited

U.S. PATENT DOCUMENTS

| | | | |
|---|---|---|---|
| 3,775,309 | 11/1973 | Ito et al. | 210/198.2 |
| 4,007,871 | 2/1977 | Jones | 210/927 X |
| 4,058,460 | 11/1977 | Ito | 210/198.2 |
| 4,151,089 | 4/1979 | Ito | 210/198.2 |

Primary Examiner—John Adee
Attorney, Agent, or Firm—Browdy and Neimark

[57] ABSTRACT

A flow-through continuous countercurrent extraction system consisting of a coiled tube or spiral coplanar channel revolving around a main axis and rotating around its own axis at the same angular velocity and in the same direction. With two solvent phases A and B, there are 5 flow tubes: (1) a feed tube for phase B located at the head end of the column, (2) a return tube for phase A located at the head end, (3) a feed tube for phase A located at the tail end, (4) a return tube for phase B located at the tail end, and (5) a sample feed tube located at the middle portion of the column. The column is mounted on a hollow rotary shaft and the axis of revolution is defined by a stationary hollow central shaft. The 5 flow tubes are led through the hollow rotary shaft, and then through the stationary central shaft. In this way, the flow tubes from the rotary shaft are allowed to rotate freely without interference or twisting. Either a single column may be used, with a counterweight, or there may be two opposite columns operating simultaneously. The ingredients of the sample are separated according to the partition coefficients; when the partition coefficients favor phase A, the solutes are eluted through the head end, and when the partition coefficients favor phase B they may be eluted through the tail end, or they may be retained in the column when the partition coefficient fall between the above values. When the operation is aimed at enrichment and/or stripping of a particular substance or substances, the sample flow tube may not be used, and the sample solution is directly introduced through the head or tail feed tube, while the enriched or stripped solution is continuously collected through either the head or tail outlet tube.

15 Claims, 10 Drawing Figures

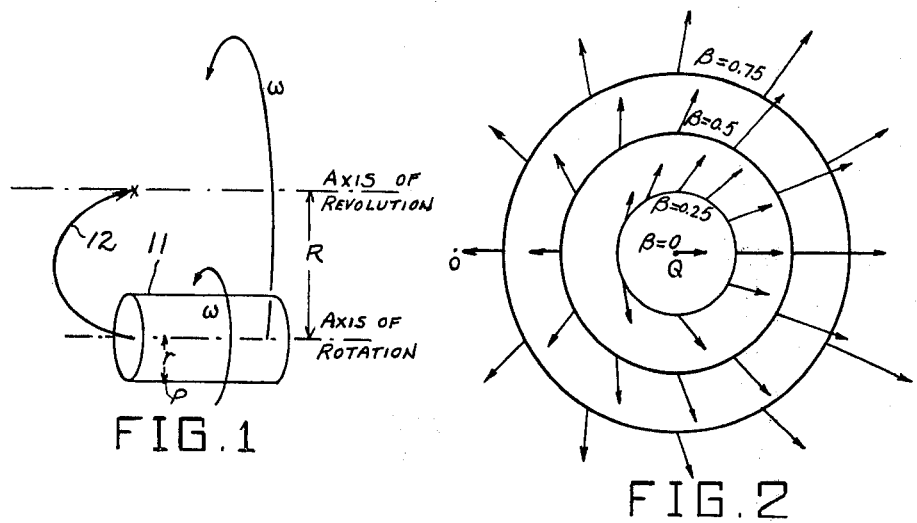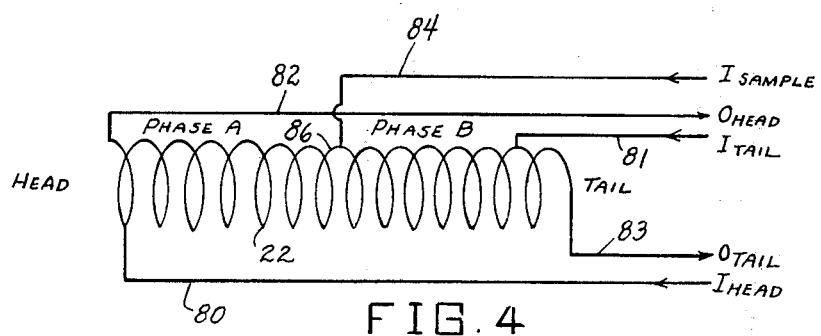

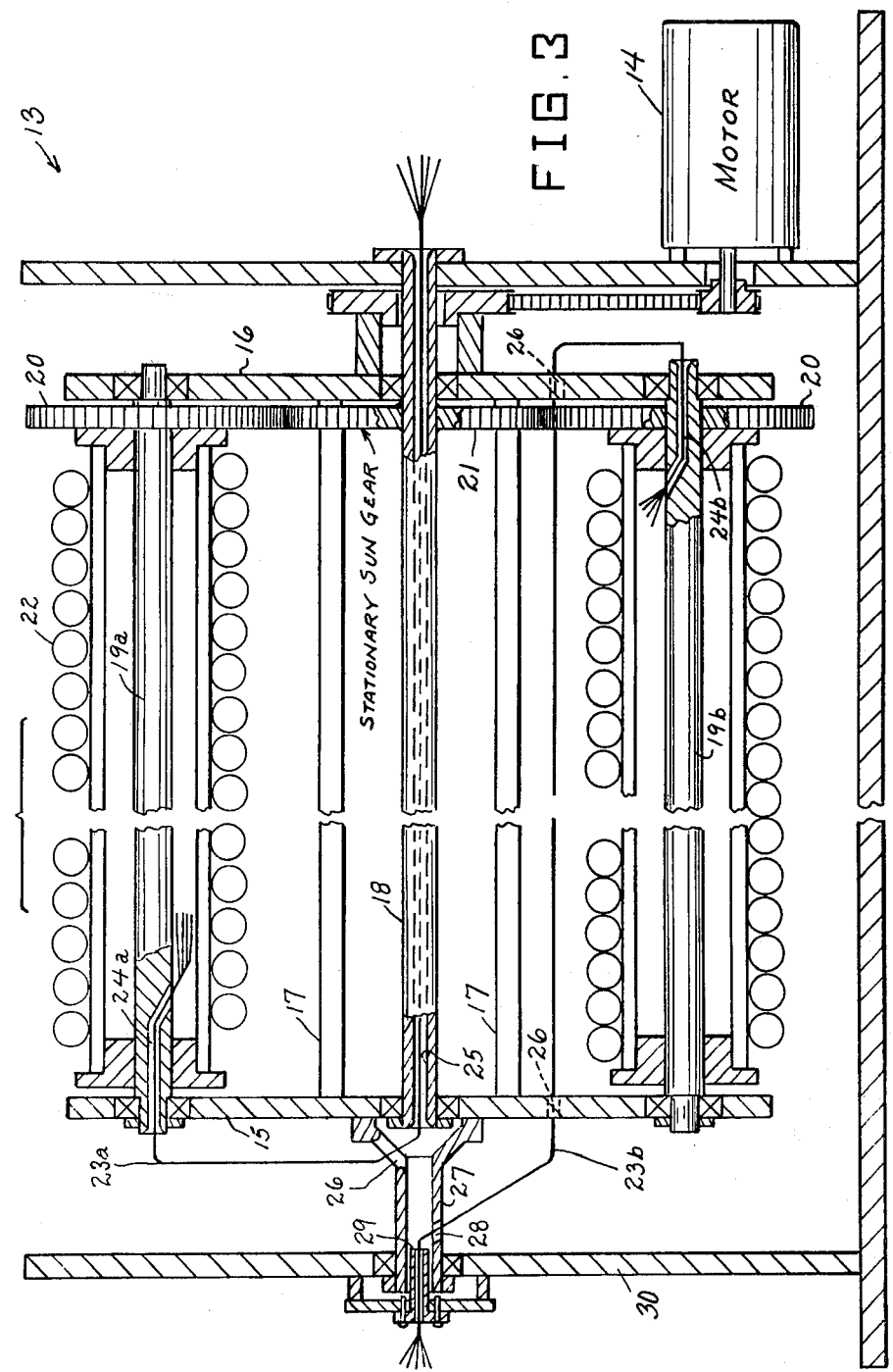

APPARATUS AND METHOD FOR CONTINUOUS COUNTERCURRENT EXTRACTION AND PARTICLE SEPARATION

This is a division, of application Ser. No. 148,491 filed May 9, 1980, now U.S. Pat. No. 4,324,661.

FIELD OF THE INVENTION

This invention relates to continuous countercurrent extraction devices and to continuous particle separation devices, and more particularly to an elution method and apparatus for continuous countercurrent chromatography and blood separation using a rotating coiled tube or conduit in an acceleration field.

BACKGROUND OF THE INVENTION

Various types of coil planet centrifuges have been developed for separating solutes and/or particles on the basis of partition coefficients and/or elutriation. Among the various schemes, the most efficient separations have been achieved from those utilizing coiled tubes rotating in an acceleration field of either gravitational or centrifugal origin. Several schemes to perform continuous countercurrent extraction have been described, such as employing a flow-through coil planet centrifuge (see U.S. Pat. No. 4,151,089 to Y. Ito) and inducing a homogeneously circulating force field around the coiled tube (see U.S. Pat. No. 3,775,309 to Y. Ito et al). A prior art arrangement providing heterogeneously circulating centrifugal force fields around the coiled tube, as utilized in the present invention, is exemplified in connection with the horizontal flow-through coil planet centrifuge disclosed in U.S. Pat. No. 4,058,460 to Y. Ito, and also in a toroidal coil planet centrifuge apparatus disclosed in U.S. patent application Ser. No. 45,052, of Y. Ito. Another system of cell separation and plasmapheresis, relative to which the present invention is an improvement and simplification, is disclosed in U.S. patent application Ser. No. 661,114, of Y. Ito, employing no rotating seals. In this system, however, a large portion of the flow tubes is subjected to revolution around the central axis of the apparatus, which limits the applicable centrifugal force field to the column.

SUMMARY OF THE INVENTION

Accordingly, a main object of the present invention is to overcome the disadvantages and deficiencies of previously employed continuous countercurrent extraction and continuous particle separation systems.

A further object of the invention is to provide a novel and improved elution method and apparatus for continuous countercurrent chromatography and blood separation using a rotating coiled tube or conduit in an acceleration field.

A still further object of the invention is to provide an improved continuous flow-through coil planet centrifuge system for separating solutes and/or particles on the basis of partition coefficients and/or elutriation which may utilize coiled tubes or conduit means rotating in an acceleration field of either gravitational or centrifugal origin, which avoids the use of rotating seals, which utilizes heterogeneously circulating centrifugal force fields around a coiled tube or conduit means, and which can be efficiently and economically employed for continuous countercurrent chromatography or for blood separation.

A still further object of the invention is to provide a novel and improved method and apparatus for performing continuous extraction of chemicals and separation of particles, which includes separation and purification of isotopes from nuclear wastes, preparative-scale separation of various chemicals, cell separation, and the like.

BRIEF DESCRIPTION OF THE DRAWINGS

Further objects and advantages of the invention will become apparent from the following description and claims, and from the accompanying drawings, wherein:

FIG. 1 is a diagrammatic view showing the orientation and motion of a coil holder undergoing a synchronous planetary motion.

FIG. 2 is a diagram showing the distribution of the relative centrifugal force fields acting on the various points on coil holders at a given moment, the diagram illustrating respective coil holders of three different beta values.

FIG. 3 is a longitudinal vertical cross-sectional view of a typical horizontal flow-through coil planet centrifuge for continuous countercurrent extraction according to the present invention.

FIG. 4 is a diagram showing the elution scheme of a helical column for continuous countercurrent extraction according to the present invention.

FIG. 5 is an enlarged cross-sectional view taken through a three-way connector and cooperating tubing employed in a typical design of a coil planet centrifuge according to the present invention to provide the inlet and outlet connections at each end of the coiled column.

DETAILED DESCRIPTION OF PREFERRED EMBODIMENTS

Figure 6:
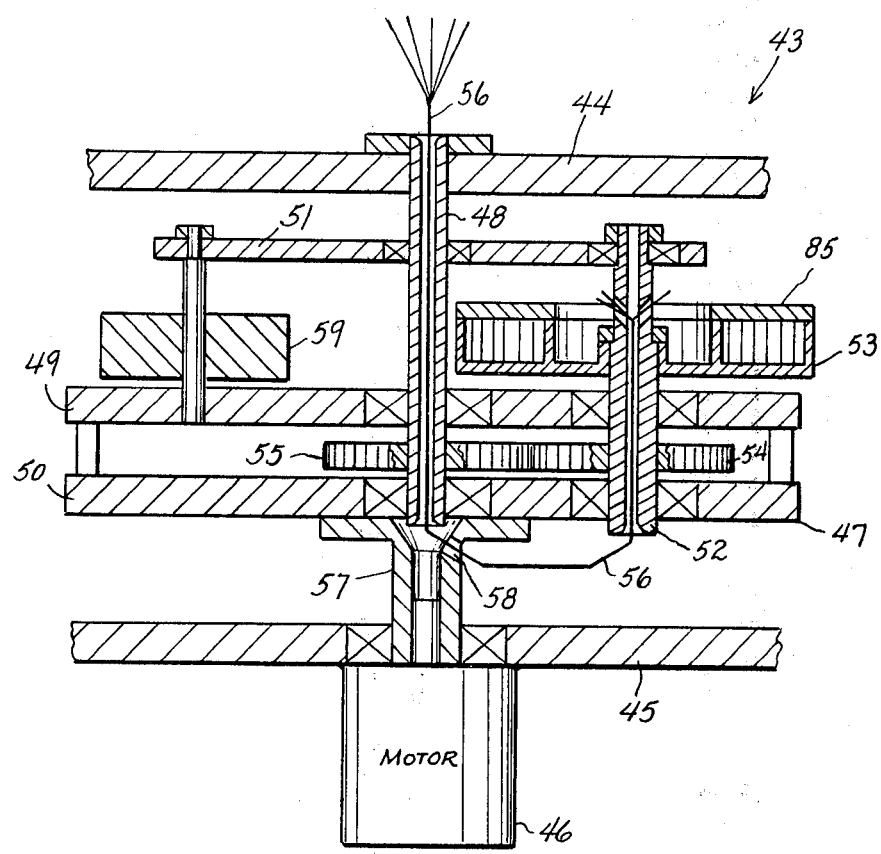
FIG. 6 is a vertical cross-sectional view of a blood cell separation apparatus according to the present invention.

Referring to the drawings, FIG. 1 diagrammatically shows the orientation and motion of a cell holder 11 undergoing a synchronous planetary motion. The holder revolves around the axis of revolution and simultaneously rotates about the axis of rotation, or its own axis, at the same angular velocity $\omega$ in the same direction. A bundle of flow tubes 12 from the holder, supported tightly at a point on the axis of revolution, as illustrated, becomes free of twisting under this particular mode of the planetary motion of the holder. Acceleration acting on an arbitrary point P on the holder located at a distance r from the axis of rotation has been analyzed. FIG. 2 shows a distribution of the relative centrifugal force fields acting on the various points on the holder at a given moment, where beta ($\beta$) denotes $r/R$, and O and Q denote the axis of revolution and the axis of rotation respectively. As is clearly illustrated, the centrifugal force vector is always directed outwardly substantially radially from the axis of rotation when the beta value is greater than 0.25, and is also heterogeneous in all directions. At a given beta value, the arbitrary point P on the holder rotates around point Q with respect to this force distribution pattern and, therefore, it experiences these fields in order during one revolutional cycle. When a tube is coiled around the holder coaxially, a particle present in the coil will travel toward one end of the coil, and this end is called the "head", while the other end is called the "tail" of the coil.

The hydrodynamic motion of the two immiscible solvent phases enclosed in such a coil is quite complex, but is easily studied by actual experiment. The results of such experiments show that in most of the cases the two phases are soon completely separated along the length of the coil. One phase occupies the head end and the other occupies the tail end of the coil. A series of experiments has been performed to determine which phase comes to the head end. The results suggest that the less viscous and lighter phase advances toward the head end of the coil. Some typical examples are listed below:

| Two-phase solvent system | Head | Tail |
| --- | --- | --- |
| Hexane/H$_2$O | upper nonaqueous | lower aqueous |
| Ethylacetate/H$_2$O | upper nonaqueous | lower aqueous |
| n-Butyl alcohol/H$_2$O | lower aqueous | upper nonaqueous |
| Blood | Red cells | Plasma |

Thus, when blood is introduced into the coil, red cells advance toward the head, and the plasma is separated at the tail end of the coil.

The separations of the two phases and/or cells are further accelerated by modifying the coiled column configuration into a spiral form. In this case, the heavier component tends to travel toward the larger diameter end and the lighter component tends to travel toward the smaller diameter end of the spiral column. Therefore, the head and tail relationship of the spiral column should be determined such that the separation of two phases or cells is promoted. For example, for the hexane/water phase system the head end should be the smaller diameter end of the spiral column, while for the blood cell separation the head end should be the larger diameter end of the spiral column.

FIg. 3 shows a horizontal flow-through centrifuge for continuous countercurrent extraction according to the present invention, designated generally at 13. In said centrifuge 13, a motor 14 drives a rotary frame consisting of a pair of rotary wings 15, 16 rigidly connected by a plurality of spaced links 17. Said frame is mounted to rotate around a stationary horizontal pipe 18, forming the central axis of the apparatus. The frame supports a pair of rotary shafts 19a, 19b, each equipped with a planetary gear 20 at one end. Each planetary gear 20 is in mesh with an identical stationary sun gear 21 rigidly mounted on the central stationary pipe 18. This gear arrangement causes each rotary shaft 19a, 19b to undergo a synchronous planetary motion, i.e., revolution around the central axis of the apparatus and rotation about its own axis at the same angular velocity ω and in the same direction, as illustrated in FIG. 1. Each column is prepared by winding a tube coaxially around a respective rotary shaft, and may be either of helical or spiral configuration. In FIG. 3 said tubes, shown at 22, are of helical configuration. The flow tubes from the rotary shaft 19a, forming a bundle 23a, are first led through an axial passage 24a of rotary shaft 19a, and then enter the bore 25 of stationary pipe 18 via a side opening 26 of a short coupling pipe 27 rigidly secured to the frame rotary wing 15 in axial alignment with the left end of stationary pipe 18, as viewed in FIG. 3. The flow tube bundle 23b from the rotary shaft 19b is similarly led through an axial passage 24b, through a pair of holes 26 in rotary wings 16 and 15, through another side hole 28 in coupling pipe 27, and through a stationary axial support tube 29 rigidly secured to a vertical fixed side member 30 forming part of the stationary supporting structure of the apparatus. The holes 26 are located some distance away from the location of gears 20 and 21. In this way, the flow tubes from each rotary shaft 19a, 19b are allowed to rotate freely without interference or twisting. The design shown in FIG. 3 allows simultaneous operation of two columns. However, when only a single column is to be used, a suitable counterweight should be mounted on the other column holder to balance the centrifuge.

FIG. 4 schematically illustrates the elution scheme of a helical column of FIG. 3 arranged for continuous countercurrent extraction. When two immiscible solvent phases A and B are confined in the coiled tube 22, the rotation of the coil separates the two phases in such a way that one phase, A, accumulates in the head end of the coil and the other, B, accumulates in the tail end. Under these circumstances, phase A, eluted through the tail end of the coil, can be collected through the head end, while phase B, eluted through the head end, can be collected through the tail end of the coil. The two phases thus undergo a countercurrent flow in the coil, and samples introduced through a sample feed tube connected to the middle portion of the coil are separated according to their partition coefficients. The solutes in the sample solution may be eluted from the head end of the coil when the values of their partition coefficients favor the phase A, may be eluted through the tail end when the values of the partition coefficients favor the phase B, or may be retained in the coil when the partition coefficients fall between the above phase-favoring values. To meet these requirements, the coiled tube is equipped with five flow tubes as follows:

flow tube $I_{head}$: feed tube for phase B, located at the head end, flow tube $O_{head}$: return tube for phase A, located at the head end, flow tube $I_{tail}$: feed tube for phase A, located at the tail end, flow tube $O_{tail}$: return tube for phase B, located at the tail end, flow tube $I_{sample}$: sample feed tube located at the middle portion of the coil.

In each operation the coil is first filled with either phase or a mixture of both phases, followed by elution of both phases through the respective inlet tubes $I_{head}$ and $I_{tail}$, while the apparatus is rotated at the optimum revolutional rate. After the steady state hydrodynamic equilibrium is established in the coil, the sample solution is fed through the flow tube $I_{sample}$ at a constant rate. When the operation is aimed at enrichment and/or stripping of a particular substance or substances, the flow tube $I_{sample}$ may not be used, and instead the sample solution is directly introduced through $I_{head}$ or $I_{tail}$, while the enriched or stripped solution is continuously collected through either $O_{head}$ or $O_{tail}$.

FIG. 5 illustrates a typical design of a combined inlet and outlet connector assembly employed at each end of the helical column. This assembly comprises a three-way connector body 31 of suitable inert material, such as Kel-F, polyethylene, or the like, connected to the end of the coil 22. The body 31 is formed with a longitudinal main bore 32 and a perpendicularly directed passage 33 communicatively connected to the intermediate portion of said main bore 32. An outlet tube 34 is connected to passage 33 by means of a conventional externally threaded flanged bushing 35 engaged in an internally threaded recess 36 coaxial with and aligned with passage 33. A similar flanged bushing 37 communicatively connects the end of coil 22 to body 31 in an internally threaded recess 38 coaxial with and aligned with main bore 32 at one end of body 31. An inlet tube 39 is communicatively connected to the other end of main bore 32 by another flanged bushing 40 engaged in an internally threaded recess 41. A relatively fine tube 42 of suitable inert plastic material is tightly received in the inlet tube 39 and extends into the coiled column tube 22 for a substantial distance, as shown. This arrangement not only simplifies the design of the column but also eliminates undesirable backflow through the outlet tube 34 of the solvent introduced from the inlet tube 39.

Blood cell separation necessitates a relatively strong centrifugal force field compared with that required for continuous countercurrent extraction. Therefore, the design of a centrifuge for this purpose should be made so as to tolerate a strong force acting on the separation bowl. The stability and durability of the centrifuge system can be greatly increased by shortening the rotary shaft and placing it in a vertical position, as in the case of an ordinary centrifuge.

FIG. 6 shows a typical design of a blood cell separator according to the present invention. The blood cell centrifuge of FIG. 6 is designated generally at 43, and its mechanism is mounted between a pair of vertically spaced, stationary horizontal support plates 44, 45. A vertical motor 46, rigidly secured to bottom plate 45, drives a rotary frame 47, via a short coupling pipe 57, around a vertical stationary pipe 48 rigidly secured to and depending from the stationary top plate 44. The rotary frame 47 comprises two spaced horizontal plates 49, 50 rigidly linked together, and an additional horizontal plate 51 spaced above and connected to plate 49, serving as a support for a vertical hollow rotary shaft 52, which in turn supports a horizontal centrifuge bowl 53 secured on said shaft 52. The shaft 52 is provided with a planetary gear 54 which meshes with an identical stationary sun gear 55 rigidly secured on the stationary vertical pipe 48. This arrangement provides the desired planetary motion of the separation bowl 53, namely, revolution around the central axis of the centrifuge and rotation about its own axis at the same angular velocity, and in the same direction. Bowl 53 is provided with a suitable detachable top cover 85.

The flow tubes from the separation bowl 53, shown as a bundle 56, are passed downwardly through the central bore of the hollow shaft 52, extend through a hole 58 in coupling pipe 57, and then extend upwardly through the bore of the stationary bearing pipe 48, thereby exiting from the top of the centrifuge.

A suitable counterweight 59 is connected between plates 51, 49 diametrically opposite bowl 53.

Figure 7:
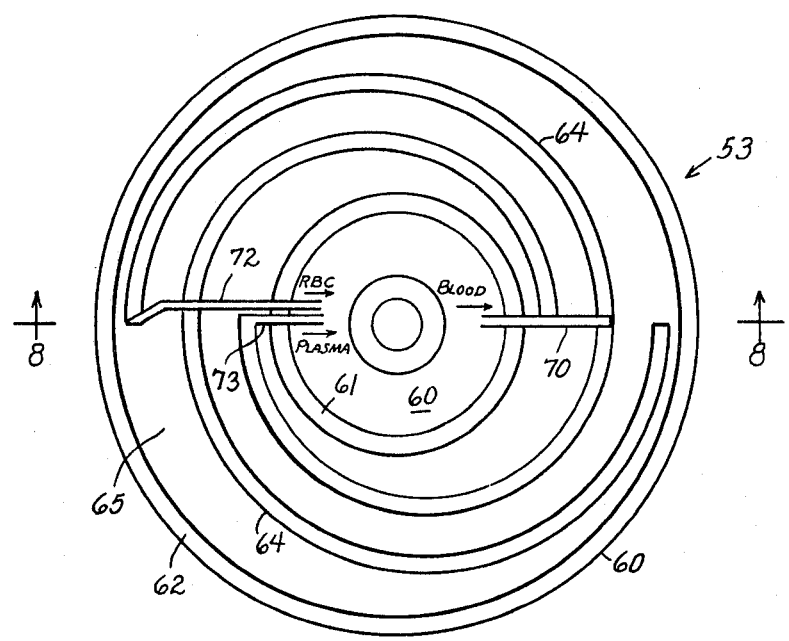
FIG. 7 is an enlarged top plan view, with its cover removed, of a separation bowl which may be employed in the apparatus of FIG. 6.
Figure 8:
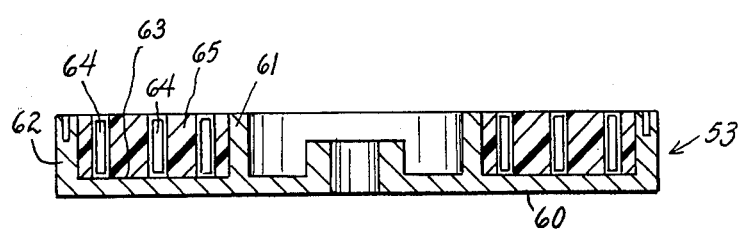
FIG. 8 is a transverse vertical cross-sectional view of the separation bowl, taken substantially on the line 8—8 of FIG. 7.

FIGS. 7 and 8 show a typical example of a design for the separation bowl 53. Said bowl 53 may comprise an aluminum, generally disc-shaped body 60 formed with upstanding concentric inner and outer annular flanges 61 and 62, defining an annular groove 63 therebetween. A pair of identical thin-walled spiral channel tubes 64,64, which may be of rectangular cross-sectional shape, are symmetrically and concentrically arranged in the annular groove 63, and the remainder of the space in said groove is filled with a light-weight rigid plastic material or plastic foam, shown at 65.

Figure 9:
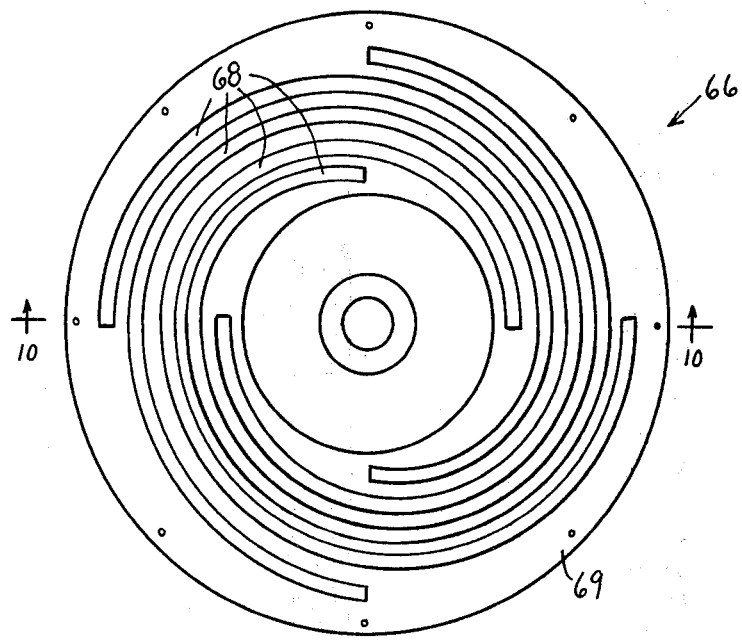
FIG. 9 is a top plan view, with its cover removed, of a modified form of separation bowl which may be employed in the apparatus of FIG. 6.
Figure 10:
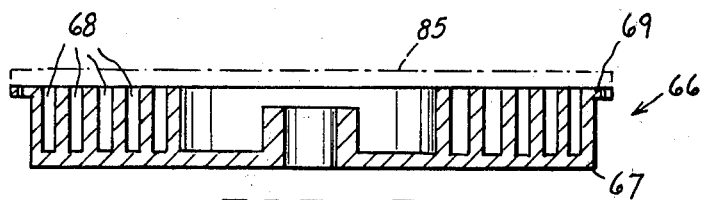
FIG. 10 is a transverse vertical cross-sectional view taken substantially on the line 10—10 of FIG. 9.

The number of spiral channels can be increased by spacing extra channels symmetrically around the periphery of the bowl. As shown in FIGS. 9 and 10, such multiple channels can be made directly in the solid aluminum bowl without the use of the plastic spacer material 65, with the advantage of reduced weight of the bowl and increased strength by using the integral metal channels. Thus, in FIGS. 9 and 10, the separation bowl is designated generally at 66, and comprises an annular aluminum bowl 67 integrally formed with four 90°-spaced concentric identical spiral channels 68. The bowl has a peripheral flange 69 to which a suitable top cover 85 may be secured. This design inherently provides increased strength to support the channels, which is desirable because of the very strong centrifugal force field.

As is diagrammatically shown in FIG. 7, during the continuous centrifugal cell separation process the blood sample is admitted via a supply tube 70 to the intermediate portion of a separation channel 64 (or 68). The red blood cells leave via an outlet tube 72 from the large-diameter end of the separation channel. The plasma leaves via an outlet tube 73 from the small-diameter end of the channel.

It will be seen that FIG. 4 diagrammatically illustrates a flow-through system covering both the helically coiled column arrangement of FIG. 3 and the spirally coiled column arrangements of FIGS. 7 and 9. In FIG. 4, a first phase (phase A) feed conduit means 80 ($I_{head}$) is connected to the column at a coil element adjacent to the head end, and a second phase (phase B) conduit means 81 ($I_{tail}$) is connected to the column at a coil element adjacent to the tail end. Second phase collection conduit means 82 (for collecting phase B, shown at $O_{head}$) is connected to the column at a coil element adjacent to the head end, and first phase collection conduit means 83 (for collecting phase A, shown at $O_{tail}$) is connected to the column at a coil element adjacent to the tail end. A sample-admission conduit means 84 (at $I_{sample}$) is connected to a coil element 86 at the middle portion of the column. As above mentioned, the separable substances in the sample may be eluted from the head end at conduit 82 of the column when the values of their partition coefficients favor phase A, or may be eluted from the tail end of the column at conduit 83 when the values of their partition coefficient favor phase B.

While specific embodiments of an improved apparatus and method for continuous countercurrent extraction and particle separation have been disclosed in the foregoing description, it will be understood that various modifications within the scope of the invention may occur to those skilled in the art. Therefore it is intended that adaptations and modifications should and are intended to be comprehended within the meaning and range of equivalents of the disclosed embodiments.

What is claimed is:

1. A flow-through countercurrent chromatographic coil planet centrifuge system comprising means defining an axially rotatable coiled column having a head end and a tail end, means to rotate said column around its own axis and simultaneously and in the same angular direction and at the same angular velocity revolve the rotating column around an axis parallel to and spaced from its own axis, first phase feed conduit means connected to said column at a coil element adjacent to said head end, second phase feed conduit means connected to said column at a coil element adjacent to said tail end, second phase collection conduit means connected to said column at a coil element adjacent to said head end, first phase collection conduit means connected to said column at a coil element adjacent to said tail end, and sample-admission conduit means connected to said column at a coil element located at an intermediate portion of said column, for separating the phases in accordance with their densities and for separating components of a sample admitted through said sample-admission conduit means in accordance with the partition coefficients of said components.

2. The flow-through countercurrent centrifuge system of claim 1, and wherein said coiled column is mounted substantially horizontally.

3. The flow-through countercurrent centrifuge system of claim 1, and wherein said coiled column is mounted substantially vertically.

4. The flow-through countercurrent centrifuge system of claim 1, and wherein said coiled column is in substantially helically-wound form.

5. The flow-through countercurrent centrifuge system of claim 1, and wherein said coiled column is in substantially spirally-wound form.

6. The flow-through countercurrent centrifuge system of claim 1, and wherein said coiled column is mounted substantially horizontally and is in helically-wound form.

7. The flow-through countercurrent centrifuge system of claim 1, and wherein said coiled column is mounted on a substantially vertical axis and is in a substantially spiral form.

8. The flow-through countercurrent centrifuge system of claim 7, and wherein said coiled column comprises a horizontal circular disc-like centrifuge bowl and wherein said coiled column comprises horizontal spiral channel means concentrically arranged in said bowl.

9. The flow-through countercurrent centrifuge system of claim 8, and wherein said channel means comprises a thin-walled spiral channel tube, and rigid filler means filling said bowl and supportingly surrounding said channel tube.

10. The flow-through countercurrent centrifuge system of claim 8, and wherein said bowl is integrally formed with a spiral horizontal groove extending around the bowl and is provided with a top cover overlying and covering the groove and defining said spiral channel means.

11. The flow-through countercurrent centrifuge system of claim 1, and wherein the system includes planetary gear means to rotate and revolve the column at the same angular velocity and in the same angular direction, whereby to avoid twisting of the conduit means.

12. The flow-through countercurrent centrifuge system of claim 1, and wherein the ratio of the radius of rotation of the coiled column to the radius of revolution of the coiled column is at least 0.25.

13. A centrifugal separator comprising a separation bowl disposed generally horizontally, means to rotate said bowl about its own generally vertically disposed axis, means to simultaneously revolve said rotating bowl about another axis spaced from and parallel to said bowl axis, said means to rotate and said means to revolve said bowl causing said bowl to revolve and to rotate about said axes in the same angular direction and at the same angular velocity, and said bowl comprising means defining at least one coiled path for containing a sample to be separated by the composite centrifugal motion to which said bowl and said sample are subjected during use of said separator, wherein said coiled path defining means comprises a thin-walled tube of rectilinear cross-sectional shape spiral-wound in said bowl, and support means for said tube comprising filler material filling said bowl all around said tube to thereby support said tube therein.

14. A centrifugal separator comprising a separation bowl disposed generally horizontally, means to rotate said bowl about its own generally vertically disposed axis, means to simultaneously revolve said rotating bowl about another axis spaced from and parallel to said bowl axis, said means to rotate and said means to revolve said bowl causing said bowl to revolve and to rotate about said axes in the same angular direction and at the same angular velocity, and said bowl comprising means defining at least one coiled path for containing a sample to be separated by the composite centrifugal motion to which said bowl and said sample are subjected during use of said separator, wherein said bowl is a circular-disc-like member, and said path defining means comprises at least one channel integrally formed in said disc-like member.

15. A centrifugal separator comprising a separation bowl disposed generally horizontally, means to rotate said bowl about its own generally vertically disposed axis, means to simultaneously revolve said rotating bowl about another axis spaced from and parallel to said bowl axis, said means to rotate and said means to revolve said bowl causing said bowl to revolve and to rotate about said axes in the same angular direction and at the same angular velocity, and said bowl comprising means defining at least one coiled path for containing a sample to be separated by the composite centrifugal motion to which said bowl and said sample are subjected during use of said separator, wherein said centrifuge is used to separate the cells and plasma in blood, said path comprising a coiled column, and means to introduce a blood sample to be separated at a middle portion of said column, wherey said simultaneous rotating and revolving of said column causes cells to collect at one end of said column and plasma to collect at the other end of said column.

* * * * *